(12) United States Patent
Roulier et al.

(10) Patent No.: US 6,303,108 B1
(45) Date of Patent: Oct. 16, 2001

(54) SOLID WARMING PULVERULENT COMPOSITION TO BE HYDRATED FOR CARING FOR OR CLEANING THE SKIN

(75) Inventors: Véronique Roulier, Paris; Thérèse Daubige, Mousseaux les Bray, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/332,900

(22) Filed: Jun. 15, 1999

(30) Foreign Application Priority Data

Jun. 15, 1998 (FR) .................................................. 98 07518

(51) Int. Cl.⁷ .................................................. A61K 7/035
(52) U.S. Cl. ............................ 424/69; 424/400; 424/401
(58) Field of Search .................................... 424/400, 401, 424/69

(56) References Cited

U.S. PATENT DOCUMENTS 5,223,559 * 6/1993 Arraudeau et al. .
5,679,326 * 10/1997 Bara et al. .
5,728,389 * 3/1998 Sebillotte-Arnaud .

FOREIGN PATENT DOCUMENTS 0 692 240 A1   1/1996   (EP) .
0 697 207 A1   2/1996   (EP) .

* cited by examiner

Primary Examiner—Thurman K. Page
Assistant Examiner—P. E. McQueeney
(74) Attorney, Agent, or Firm—Oblon, Spivak, McClelland, Maier & Neustadt, P.C.

(57) ABSTRACT

A warming and foaming anhydrous pulverulent composition, which is capable of being, hydrated, which comprises cosmetically acceptable powder and a binder, where the powder comprises solid particles of expanded polymers and the binder comprises an effective amount of an agent capable of giving off heat during hydration. The composition may be used, for example, for cleaning and/or caring for human skin.

33 Claims, No Drawings

SOLID WARMING PULVERULENT COMPOSITION TO BE HYDRATED FOR CARING FOR OR CLEANING THE SKIN

BACKGROUND OF THE INVENTION

1. Field of the Invention

The present invention relates to a warming and foaming anhydrous pulverulent composition, having a deformable solid appearance. The composition may be used, for example, for cleaning in depth and/or caring for the skin. This composition may be applied both to the human face and to the human body, and may have a very soft feel. This composition, with a dry feel, may be hydrated before use. The present invention also relates to a process for cleaning and/or caring for the skin.

2. Description of the Background

Cleaning compositions for the skin are usually provided in the form of solid bars, such as soaps, or in the form of more or less viscous liquids.

In cleaning with a soap, consumers generally make use of the whole soap. In point of fact, soap has a tendency to soften as it is used, due to its contact with water, and to age badly. In addition, it is often the case that it breaks up and that consumers find themselves with small bits of soap which are difficult to use. Furthermore, a wet soap is generally slippery, which makes it difficult to use, in particular for young children. For this reason, it has become common to use liquid cleaners in place of soaps. Unfortunately, the more liquid the compositions, the more difficult it is to measure them out, in particular because they have a tendency to escape between the fingers, and the more they have a tendency to escape from their packaging, which can be a great nuisance when they come into contact with clothing.

It is also known to use cleansing masks for the deep cleaning of the face. These masks are generally provided in the form of a gel or cream, to be applied as a thin layer over the skins comprising powders capable of absorbing the fatty substances produced by the skin, such as sebum. These masks can optionally comprise cosmetic or dermatological active agents of the skin for completing the cleaning and/or contributing well-being to the skin. Such masks are disclosed in particular in U.S. Pat. No. 5,690,945 and WO-A-86/05394. These masks are often heavy to wear and not very comfortable (tightness) and the cleaning is not always felt to be effective. Furthermore, these masks are difficult to rinse off.

Moreover, users are increasingly looking for novel textures and novel types of product. Accordingly, there remains a need for novel compositions for cleaning and/or caring for human skin.

SUMMARY OF THE INVENTION

It is an object of the present invention to provide compositions which may be used to clean and/or care for human skin, which overcome the disadvantages discussed above.

It is another object of the present invention to provide methods of cleaning and/or caring for human skin with the inventive compositions.

It is another of the present invention to provide methods for making the inventive compositions.

The objects of the present invention, and others, may be accomplished with a warming anhydrous pulverulent composition, which is capable being hydrated and suitable for cleaning and/or caring for the skin, comprising:

(a) a cosmetically acceptable powder comprising solid particles of an expanded polymer, and
(b) a cosmetically acceptable binder comprising an effective amount of an agent capable of giving off heat during hydration.

This composition is a warming and foaming anhydrous composition which is easy to apply, which is very light, which has great softness and which gives an effect of well-being after application. In addition, it has the advantage of rinsing off in an outstanding way and of exhibiting an entirely unusual texture.

The objects of the invention may also be accomplished with a method of a method of cleaning and/or caring for human skin, by applying the inventive composition to the skin.

The objects of the invention may also be accomplished with a method of cleaning and/or caring for human skin, comprising contacting the inventive composition with water, to hydrate the composition, causing the composition to foam, and then applying the hydrated composition to the skin.

The objects of the invention may also be accomplished with a method of cleaning land/or caring for human skin, comprising contacting the inventive composition with water, to hydrate the composition, and then applying the hydrated composition to the skin.

The objects of the invention may also be accomplished with a method of preparing the inventive composition, comprising combining (a) and (b).

A more complete appreciation of the invention and many of the attendant advantages thereof will be readily obtained as the same becomes better understood by reference to the following detailed description.

DETAILED DESCRIPTION OF THE INVENTION

The term "warming: composition" as used herein refers to a composition where the user experiences warming during the application of the hydrated composition on the skin. A warming composition is where contacting the anhydrous composition cold water (having a temperature less than 37° C.), causes an instantaneous rise in the temperature of the composition from several degrees (one to ten degrees).

As will be readily appreciated, the term "anhydrous" as used herein refers to a composition which is free of added water. The composition may contain relatively small amounts of water which may be present in the constituents of the composition. A feature of the inventive composition is that it is anhydrous. Upon contact with water, the composition becomes hydrated. During hydration the composition warms by the release of heat.

The composition of the invention may be used to clean and/or care for human skin, such as facial and/or body skin. The composition is especially useful for cleaning and/or caring for the human face. The composition is provided in the form of a deformable or malleable dry solid which does not stain and which resembles marshmallow (see U.S. Pat. No. 3,682,659, incorporated herein by reference, for the consistency of marshmallow). This solid can be modeled like children's plasticine. It can be easily broken by hand in order to remove only the necessary amount of product. In particular, the composition may be packaged in single-dose form, which is particularly advantageous from the viewpoint of hygiene, for example in the form of small cubes, of balls or in the form of tetrahedra.

By virtue of this solid texture there is no risk of the composition of the invention escaping from its packaging, in particular during transportation. Furthermore, this composition is very easy to grasp and does not flow between the fingers; it is much simpler to measure out than standard liquid cleaners and the problem of wear of hard soaps does not exist. Furthermore, it is easy, light and pleasant to apply. Moreover, its storage does not present any problems and its contamination by the surroundings and/or the handling by the consumer is relatively reduced and in any event much less than that of the known products. In particular, it is not necessary to introduce a preservative in order to provide for its antimicrobial protection.

Without being limited to any particular theory, the deformable solid texture of the inventive composition is believed to be due mainly to the powder.

For the purpose of obtaining a solid with a pleasant and soft touch, it is preferable to use powder particles having a particle size of 1 $\mu$m to 300 $\mu$m, for example of 5 $\mu$m to 200 $\mu$m and preferably of 10 $\mu$m to 100 $\mu$m and better still of 15 $\mu$m to 40 $\mu$m. These ranges include all specific values and subranges therebetween including 2, 20, 25, 30, 50, 75, 100, 150 and 250 $\mu$m.

The great softness contributed by these particles makes it possible for consumers with sensitive skin to use the composition of the invention without difficulty.

By virtue of the presence of the agent capable of giving off heat in the composition, cleaning takes place in depth, owing to excretion of the fatty substances and impurities being facilitated by an opening of the pores of the skin. These impurities and fatty substances are absorbed by the powder as they emerge from the skin, without, however, drying and tightening the skin.

In order to confer a light and airy appearance on the composition of the invention, the particles preferably have a relative density of less than 0.09, and more preferably of less than 0.06 and most preferably of less than 0.04. These ranges include all specific values and subranges therebetween such as less than 0.08, 0.07 and 0.05.

For the purpose of obtaining this low relative density, use is advantageously made of hollow particles filled with a gas. This gas can be air, nitrogen, isobutane, isopentane, and the like.

In one embodiment of the invention, the particles are provided in the form of beads. However, it is possible to use particles having the form of fibers.

These particles may be prepared from different inert materials which do not react chemically with the cosmetically acceptable binder. In particular, these particles do not react with the oils, the surfactants and the various other constituents of the composition, such as the active agents.

The powder of the invention, which confers the deformable solid texture, has the distinguishing feature of readily disintegrating by simple dilution in a solvent, such as water optionally containing salts or trace elements.

As a method for evaluating a powder for use in the inventive composition, the following simple test may be conducted:

(1) add the particles to water comprising a dye conventionally used in the cleaning field, such as the disodium salt of Brilliant Blue FCF, listed in the Color Index under the reference CI 42090, until a colored paste is obtained, and (2) pour a drop of water onto the paste.

When the paste at the point of impact of the water drop is much lighter in color than the remainder of the paste, this means that the particles under consideration are appropriate for texturizing the composition. Conversely, when the paste at the point of impact has not lightened in color, the particles under consideration are in not appropriate.

The inert particles are advantageously prepared from thermoplastic materials, such as optionally expanded polymers or copolymers of acrylonitrile, of vinylidene chloride, of vinyl chloride and/or of acrylic or styrene monomer. The acrylic monomer is, for example, a methyl or ethyl acrylate or methacrylate. The styrene monomer is, for example, α-methylstyrene or styrene.

The particles are preferably hollow deformable particles of expanded copolymer of vinylidene chloride and of acrylonitrile or of vinylidene chloride, of acrylonitrile and of methacrylate. Use may be made, for example, of a copolymer comprising: from 0% to 60% of units derived from vinylidene chloride, from 20% to 90% of units derived from acrylonitrile and from 0% to 50% of units derived from an acrylic or styrene monomer, the sum of the percentages (by weight) being equal to 100. These particles are provided in particular in the dry or hydrated state and can be obtained, for example, according to the processes described in EP-A-56,219, EP-A-348,572, EP-A-320,473, EP-A-112,807 and U.S. Pat. No. 3,615,972, all of which are incorporated herein by reference.

These hollow particles can be, for example, those formed of a terpolymer of vinylidene chloride, of acrylonitrile and of methacrylate sold under the tradename Expancel by Nobel Casco under the references 551 DE 12 (particle size of approximately 12 $\mu$m and density 40 kg/m$^3$), 551 DE 20 (particle size of approximately 30 $\mu$m and density 65 kg/m$^3$) or 551 DE 50 (particle size of approximately 40 $\mu$m). Mention may also be made of the microspheres formed of the same expanded terpolymer in the dry state having a particle size of approximately 18 $\mu$m and a density of approximately 60 to 80 kg/m$^3$, known hereinbelow as EL 23, or having a particle size of approximately 34 $\mu$m and a density of approximately 20 kg/m$^3$, described hereinbelow as EL 43, or having a particle size of approximately 150 $\mu$m, described hereinbelow as EL 55.

On the other hand, particles of maize starch, of pyrogenic silica, of polyethylene, of polyurethane or of polyester, which is non-expanded, do not make it possible to obtain a solid composition which is properly removed from the skin during rinsing.

Whether or not a deformable solid is obtained is related to the amount of powder or structuring agent used in the composition; above a certain amount of particles, known as critical pigment volume concentration (CPVC), a sudden increase in the viscosity of the medium is noticed. The CPVC depends on the medium and on the nature of the particles; it therefore has to be determined each time. Determining the CPVC is routine for one skilled in the art. For example, the official ASTM method may be used to determine the CPVC.

In practice, the structuring powder represents up to 80% by volume of the composition, of which advantageously 60% represent particles having a relative density of less than 1. The range of the volume % of the powder in the composition includes all specific values and subranges therebetween, such as 1, 2, 5, 10, 15, 20, 25, 30, 40, 50, 60 and 70%.

The binder may represent up to 20% by volume of the composition. In particular, the particles with a relative density of less than 1 represent from 2 to 20% and better still from 3 to 7% of the total weight of the composition. The volume % of the binder in the composition includes all specific values and subranges therebetween, such as 0.5, 1, 2, 5, 8, 10, 12, 15 and 18%.

The composition of the invention comprises, in addition to the structuring particles, an effective amount of an agent capable of giving off heat during the hydration of the composition. This agent is selected, in particular, from polyols having at least 2 hydroxyl groups and at least 3 carbon atoms, such as, in particular, glycerol, diglycerol, propylene glycol, butylene glycol, a polyethylene glycol with a molecular weight of less than 600, such as a PEG 400 sold by BASF under the name Lutrol E400, sugars, such as sorbitol, or their mixtures. This type of agent exhibits the distinguishing feature of reacting chemically with water according to an exothermic process. In order for this exothermic process to take place, it is desirable for the composition to be devoid of water, as described above.

The amount of this agent must be such that the user effectively experiences warming during the application of the composition after hydration. In practice, the warming agent represents from 20 to 85% of the total weight of the composition and better still from 33 to 67%. These ranges include all specific values and subranges therebetween, such as 25, 30, 35, 40, 50, 60, 70, 75 and 80% by weight.

The composition according to the invention may advantageously comprise one or more cleaning and/or foaming anhydrous surfactants which can be non-ionic, anionic, cationic and/or amphoteric surfactants. They can be used in an amount ranging, for example, from 10% to 60% of the total weight of the composition and preferably from 30% to 60%. These ranges include all specific values and subranges therebetween, such as 15, 20, 25, 35, 40, 45, 50 and 55% by weight. The anhydrous surfactant or surfactants are advantageously in the powder form. The surfactant may have a particle size ranging from 5 to 50 µm and better still from 10 to 20 µm.

Non-ionic surfactants which may be used in the invention include, for example, the condensates of alkylene oxides and of alkylphenols, such as ethoxylated octylphenol, for example that sold under the name Triton X45 by Rohm and Haas, the condensates of ethylene oxide, of propylene oxide and of ethylenediamine, alkylpolyglucosides, ethers of fatty alcohols and polyols, such as, for example, Polyglyceryl-3 hydroxylauryl ether (CTFA name), sold under the name Chimexane NF by Chimex, or mixtures thereof.

Anionic surfactants which may be used in the compositions include, for example. polyalkylene glycols ether of fatty alcohols, taurates, acyl lactylates, such as sodium stearoyl lactylate (for example Pationic SSL, sold by Maprecos), alkyl sulphates, such as sodium lauryl sulphate (Sipon LCS, sold by Henkel), glyceryl alkyl sulphates, such as sodium cocoglyceryl sulphate (sold by Nikko under the name Nikkol SGC-80N), polyoxyethylenated alkyl sulphates, alkyl ether sulphates, such as monoethanolamine lauryl ether sulphate, alkyl ether carboxylates, monoalkyl or dialkyl phosphates, such as the mono(2-hexyldecyl) phosphate of argine (C6C10 MAP-1-ARG, sold by Kao Chemicals), ethoxylated alkyl phosphates, N-acyl sarcosinates, such as sodium myristoyl sarcosinate (for example Nikkol Sarcosinate MN, sold by Nikko), N-acyl glutamates, such as sodium lauroyl glutamate (for example Amisoft LS11, sold by Ajinomoto), acyl isethionates, such as sodium cocoyl isethionate, sold in particular by Jordan (Jordapon CI), polysorbates, succinamates, soaps, such as potassium laurate, myristate, palmitate or stearate, or mixtures thereof.

Mention may be made, as amphoteric or zwitterionic surfactants, of, for example, betaines and betaine derivatives, sultaines and sultaine derivatives, imidazolinium derivatives, such as disodium cocoamphodiacetate, or mixtures thereof.

Mention may be made, as cationic surfactants which can be used in the invention, of pyrrolidone—carboxylate derivatives, such as PCA ethyl cocoyl arginate (Cation CAE, sold by Ajinomoto).

In addition, the composition according to the invention may also comprise one or more oils which can be used in an amount ranging from 0% to 30% by weight and preferably from 0% to 10% of the total weight of the composition. These ranges include all specific values and subranges therebetween, such as 0.5, 1, 2, 3, 5, 8, 10, 15, 20 and 25% by weight. These oils form an integral part of the binder.

The oils which can be used in the composition according to the invention can be selected from mineral oils, such as liquid paraffin and liquid petrolatum; oils of animal origin, such as perhydrosqualene; those of vegetable origin, such as sweet almond oil, avocado oil, castor oil, olive oil, jojoba oil, sesame oil, groundnut oil, grape seed oil, rapeseed oil, coconut oil, hazelnut oil, palm oil, apricot kernel oil, calophyllum oil, rice bran oil, maize germ oil, wheat germ oil, soybean oil, sunflower oil, safflower oil, passion flower oil, rye oil and karite butter and its liquid fraction; synthetic oils, such as fatty esters, for example butyl or isopropyl myristate, hexadecyl, isopropyl, octyl or isodecyl stearate, decyl oleate, hexyl laurate, propylene glycol dicaprylate, esters derived from lanoic acid, such as isopropyl lanolate and isocetyl lanolate, isoparaffins, acetylglycerides, octanoates of alcohols and of polyalcohols, such as those of glycol and glycerol, ricinoleates of alcohols and of polyalcohols, or fatty acid triglycerides; silicone oils, such as cyclomethicones or polydimethylsiloxanes which are volatile and/or non-volatile, or phenyldimethylsiloxanes; or their mixtures.

In addition, the composition may also comprise one or more other lipophilic ingredients conventionally used in cleaning and/or care compositions. These ingredients are in particular screening agents, fragrances, preservatives, antioxidants, pH-regulating agents, sequestering agents, fillers, dyes, cosmetic or dermatological active agents, or their mixtures. These adjuvants are used in the usual proportions for cleaning and/or care compositions, for example from 0.01 to 10% of the total weight of the composition. This range includes all specific values and subranges therebetween, including 0.05, 1, 2, 5 and 8% by weight. These adjuvants must be of such a nature and used in such an amount that they do not disturb the properties desired for the composition of the invention.

Mention may be made, as active agents which can be used in the invention, of antibacterials, such as octopirox and triclosan, keratolytic agents, such as salicylic acid, essential oils or lipophilic vitamins.

The composition according to the invention can be prepared by any means known to a person skilled in the art and, in particular, by simple mixing of the various constituents and molding in an appropriate mold. However, it is advantageously prepared by mixing, followed by kneading and then by extrusion in an extruder, preferably a twin-screw extruder, such as those disclosed EP-A-605,284 and FR-A-2,715,306, both incorporated herein by reference, in which the two screws rotate in the same direction. Use may also be made of the process disclosed in the EP-A-651,991, incorporated herein by reference.

A further subject-matter of the invention is a process for the preparation of the above composition, which consists in introducing the various constituents of the composition into an extruder, in then kneading them therein, and in shaping the mixture obtained.

The various constituents of the composition are introduced at room temperature, preferably at approximately 20°

C., at the inlet of the twin-screw extruder in the feed region. Preferably, the solid constituents are introduced at the head of the extruder and then the liquid constituents are introduced laterally. The combined mixture is kneaded in various regions of the extruder, which are maintained at a temperature preferably ranging from 15 to 25° C.; the mass obtained is subsequently transported towards the outlet of the extruder and extruded through a die. The rotational speed of the screws is of the order of 400 to 1000 revolutions/minute, preferably of between 550 and 650 revolutions/minute.

The extruded mass exits from the die in the form of sausages, with a diameter given according to the die used, which can subsequently be cut up and shaped, in particular in the form of a solid bar or stick. Other forms can, of course, be prepared by choosing appropriate dies and devices for shaping the final products which are suited to the desired form.

The extruded mass can also be dehydrated and/or milled and/or compacted. Dehydration is advantageously used when the constituents of the composition are introduced in the form of a solution or dispersion in aqueous medium.

Since the entire extrusion process is carried out at room temperature, of the order of 20–25° C., it is possible to use heat-sensitive ingredients of the vitamin or volatile oil type.

Furthermore, the heat-sensitive ingredients can be introduced in any region of the extruder (at the head, in the middle or at the end), since no decomposition due to heat is to be feared. This is particularly advantageous for the introduction of structuring agents of the Expancel type.

It is also possible to carry out part of the extrusion under an inert gas (for example, nitrogen).

The compositions of the present invention may be used for cleaning and/or caring for human skin. Thus, a further subject-matter of the invention is a cosmetic process for cleaning and/or caring for the skin, which consists in hydrating a composition as defined above, in causing it to foam, in applying it to the skin and, finally, in rinsing the skin. In these methods, the composition is contacted with water. This contact results in hydration of the composition, with the generation of heat. The hydrated composition may then be applied in an effective amount to the skin to be treated. After the appropriate treatment time, the composition may be removed from the skin by washing with water.

Having generally described this invention, a further understanding can be obtained by reference to certain specific examples which are provided herein for purposes of illustration only and are not intended to be limiting unless otherwise specified.

EXAMPLES

In the Examples below, the amounts used are % by weight.

Example 1
Warming and Foaming Pulverulent Composition for Greasy Skin with a Tendency Towards Acne

| Sodium cocoyl isethionate (Jordapon CI, sold by Jordan) | 44.0% |
|---|---|
| Glycerol | 50.0% |
| Preservative | q.s. |
| Octopirox | 0.1% |

-continued

| Fragrance | q.s. |
|---|---|
| Salicylic acid | 0.5% |
| Expancel 551 DE 20 | 5.0% |

The procedure consists in introducing, under cold conditions, the surfactant and the glycerol at the head of a twin-screw extruder and in then introducing laterally, in the various stages of the extruder, the active agents, the preservatives, the fragrance and, at the end, the Expancel. The mixture is extruded under cold conditions until a homogeneous paste is obtained, which paste is subsequently shaped in an appropriate die in order to produce a sausage which is cut up into sticks.

The product obtained is a white non-sticky paste which can be easily modeled, which can be easily wetted or hydrated, which is easy to apply and remove, which is soft to the touch and which has a good foaming power.

This product can then be hydrated and then kneaded until it foams, in particular in the hollow of the hand. The foam obtained is then applied as a thin layer to the skin of the face. The amount of water can represent from 6 to 10 times by volume that of the sample taken for the cleaning.

From the time of the application of the foam to the face, a slight release of heat is felt, providing for the opening of the pores of the skin and the release of the impurities. The anti-acne active agents subsequently penetrate into the skin in order to clean it in depth and to disinfect it for the purpose of preventing the formation of spots. The composition is easily removed with water.

Example 2
Warming and Foaming Composition for Any Skin Type

| Sodium cocoyl isethionate (Jordapon CI, sold by Jordan) | 55.0% |
|---|---|
| Expancel 551 DE 20 | 5.0% |
| PEG 400 | 40.0% |

The procedure is the same as for Example 1 and a paste is obtained which has analogous properties.

Example 3
Warning and Foaming Comprisition for Sensitive Skin

| Sodium cocoyl isethionate (Jordapon CI, sold by Jordan) | 36.0% |
|---|---|
| Glycerol | 57.0% |
| Sweet almond oil | 1.0% |
| Microspheres EL 23 | 6.0% |

The procedure is the same as for Example 1 and a paste is obtained which has analogous properties.

Obviously, numerous modifications and variations of the present invention are possible in light of the above teachings. It is therefore to be understood that within the scope of the appended claims, the invention may be practiced otherwise than as specifically described herein.

This Application is based on French Application Serial No. 98-07518, filed in Jun. 15, 1998, and incorporated herein by reference.

What is claimed is:

1. An anhydrous pulverulent composition for cleaning or caring for the skin or both, comprising:

a) a cosmetically acceptable powder comprising solid particles of an expanded polymer; and
b) a cosmetically acceptable binder comprising an amount of a polyol having at least two hydroxyl groups effective to release heat during hydration, said polyol which releases heat during hydration comprising 20 to 85% of the total weight of the composition;

wherein the composition is hydrated upon contact with water and thereby produces heat.

2. The composition of claim 1, wherein the solid particles have a particle size of 1 μm to 300 μm.

3. The composition of claim 2, wherein the solid particles have a particle size of 10 μm to 100 μm.

4. The composition of claim 3, wherein the solid particles have a particle size of 15 μm to 40 μm.

5. The composition of claim 1, wherein the solid particles have a relative density of less than 0.09.

6. The composition of claim 5, wherein the solid particles have a relative density of less than 0.04.

7. The composition of claim 1, wherein the solid particles are present at a concentration at least equal to a critical pigment volume concentration.

8. The composition of claim 1, wherein the solid particles are hollow.

9. The composition of claim 8, wherein the solid, hollow particles contain a gas.

10. The composition of claim 1, wherein the solid particles are composed of a thermoplastic material.

11. The composition of claim 9, wherein the gas is selected from the group consisting of air, nitrogen, isobutane and isopentane.

12. The composition of claim 1, wherein the solid particles are composed of a material selected from the group consisting of polymers and copolymers of vinylidene chloride, vinyl chloride, acrylonitrile, acrylic monomers, and styrene monomer.

13. The composition of claim 1, further comprising at least one foaming or cleaning anhydrous surfactant or both.

14. The composition of claim 1, wherein the polyol which produces heat is selected from the group consisting of glycerol, diglycerol, polyethylene glycols, propylene or butylene glycol, sugars, and mixtures thereof.

15. The composition of claim 1, wherein the polyol which produces heat comprises 33 to 67% of the total weight of the composition.

16. The composition of claim 13, wherein the surfactant is in powder form.

17. The composition of claim 13, wherein the surfactant is sodium cocoyl isethionate.

18. The composition of claim 13, wherein the surfactant comprises 10 to 60% of the total weight of the composition.

19. The composition of claim 18, wherein the surfactant comprises 30% to 60% of the total weight of the composition.

20. The composition of claim 1, further comprising at least one lipophilic ingredient selected from the group consisting of screening agents, fragrances, preservatives, antioxidants, pH-regulating agents, sequestering agents, fillers, dyes, cosmetic or dermatological active agents, and mixtures thereof.

21. The composition of claim 1, which is in the form of a deformable solid.

22. The composition of claim 1, which is obtained by extrusion under cold conditions.

23. The composition of claim 1, wherein the solid particles are in the form of beads.

24. The composition of claim 1, wherein said heat released during hydration is from 1 to 10° C. when contacted with water having a temperature of less than 37° C.

25. A method of cleaning or caring for human skin or both, comprising applying the composition of claim 1, to human skin.

26. A method of cleaning or caring for human skin or both, comprising contacting the composition of claim 1, with water, thereby hydrating the composition, causing the composition to foam, and then applying the hydrated composition to the skin.

27. The method of claim 26, further comprising rinsing the skin after applying the hydrated composition to the skin.

28. The method of claim 26, wherein said composition when contacted with water having a temperature of less than 37° C., causes an instantaneous increase in temperature of 1 to 10° C.

29. A method of cleaning or caring for human skin or both, comprising contacting the composition of claim 1, with water, thereby hydrating the composition, and then applying the hydrated composition to the skin.

30. The method of claim 29, further comprising rinsing the skin after applying the hydrated composition to the skin.

31. The method of claim 29, wherein said composition when contacted with water having a temperature of less than 37° C., causes an instantaneous increase in temperature of 1 to 10° C.

32. A method of preparing the composition of claim 1, comprising mixing a) with b).

33. The method of claim 32, which further comprises kneading the formed mixture, and extruding the mixture.

* * * * *